United States Patent
Mohseni et al.

(10) Patent No.: US 6,242,007 B1
(45) Date of Patent: *Jun. 5, 2001

(54) NON-SPHERICAL AND NON-PLATELET FORMS OF PYRITHIONE SALTS AND METHODS OF MAKING SAME

(75) Inventors: Saeed H. Mohseni, Fairport; John J. Jardas, Rochester, both of NY (US); George Polson, Harwinton, CT (US); David C. Beaty, Bergen; Charles W. Kaufman, Rochester, both of NY (US)

(73) Assignee: Arch Chemicals, Inc., Norwalk, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/410,687

(22) Filed: Oct. 1, 1999

Related U.S. Application Data

(63) Continuation-in-part of application No. 09/025,665, filed on Feb. 18, 1998, now Pat. No. 6,017,562.
(60) Provisional application No. 60/044,339, filed on Apr. 28, 1997.

(51) Int. Cl.[7] .............................. A61K 7/06; A61K 9/14; A01N 5/02
(52) U.S. Cl. ................ 424/489; 424/70.1; 424/401; 514/188; 514/345
(58) Field of Search .................... 424/489, 70.1, 424/401; 252/363.5; 514/937, 188, 345

(56) References Cited

U.S. PATENT DOCUMENTS

| | | | |
|---|---|---|---|
| 2,786,847 | 3/1957 | Cislak | 260/294.8 |
| 2,809,971 | 10/1957 | Bernstein et al. | 260/270 |
| 3,589,999 | 6/1971 | McRae et al. | 210/28 |
| 3,590,035 | 6/1971 | Damico | 260/290 |
| 3,773,770 | 11/1973 | Damico | 260/290 |
| 4,396,766 | 8/1983 | Farmer, Jr. et al. | . |
| 4,632,991 | 12/1986 | Maurer et al. | 546/6 |
| 4,659,830 | 4/1987 | Maurer et al. | 546/6 |
| 4,670,430 | 6/1987 | Imamura et al. | 514/188 |
| 4,940,578 | 7/1990 | Yoshihara et al. | 424/70 |
| 5,540,860 | 7/1996 | Hosseini et al. | 252/308 |
| 5,562,995 | 10/1996 | Kappock et al. | . |
| 5,614,538 | 3/1997 | Nelson | 514/345 |
| 5,650,095 | 7/1997 | Hosseini et al. | 252/308 |
| 5,675,013 | 10/1997 | Hani et al. | 514/348 |
| 5,696,083 | 12/1997 | Nelson | 514/845 |
| 5,707,929 | 1/1998 | Kuusisto et al. | . |
| 5,723,112 | 3/1998 | Bowser et al. | . |
| 6,017,936 | * 1/2000 | Polson et al. | 514/345 |

FOREIGN PATENT DOCUMENTS 2 282 533  * 12/1995 (GB).
99/66886  * 12/1999 (WO).

* cited by examiner

*Primary Examiner*—Thurman K. Page
*Assistant Examiner*—Brian K. Seidleck
(74) *Attorney, Agent, or Firm*—Todd E. Garabedian; Dale L. Carlson; Wiggin & Dana

(57) ABSTRACT

The present invention relates to non-spherical and/or non-platelet pyrithione particles. Also disclosed is a method for producing non-spherical and/or non-platelet particles of pyrithione salts, comprising reacting pyrithione acid or a water-soluble salt of pyrithione and a water-soluble polyvalent metal salt in the presence of an ionic surfactant composition at temperature from about 20° C. to about 60° C. and at a pH from 4–9 to produce non-spherical and/or non-platelet particles of pyrithione salts. The present invention further relates to particles made by the above methods and products, such as shampoos, soaps, and skin-care medicaments made using these particles.

34 Claims, 2 Drawing Sheets

NON-SPHERICAL AND NON-PLATELET FORMS OF PYRITHIONE SALTS AND METHODS OF MAKING SAME

This application is a Continuation-in-Part application of U.S. Ser. No. 09/025,665 filed Feb. 18, 1998, now U.S. Pat. No. 6,017,562, which claims the benefit of Provisional Application Ser. No. 60/044,339 filed Apr. 28, 1997.

BACKGROUND OF THE INVENTION

1. Field of the Invention

The present invention relates generally to method for preparing particles of pyrithione salts, and more specifically to methods of preparing particles of pyrithione salts having non-spherical or non-platelet forms, particularly needle or rod forms, in the presence of ionic surfactants or a combination of ionic and nonionic surfactants. The present invention also relates to products made with the non-spherical or non-platelet particles of pyrithione salts.

2. Description of the Related Art

Polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide) are known to be effective biocidal agents, and are widely used as fungicides and bacteriocides in paints and personal care products such as anti-dandruff shampoos. The polyvalent metal salts of pyrithione are only sparingly soluble in water and include magnesium pyrithione, barium pyrithione, bismuth pyrithione, strontium pyrithione, copper pyrithione, zinc pyrithione, cadmium pyrithione, and zirconium pyrithione. The most widely used divalent pyrithione salts are zinc pyrithione and copper pyrithione.

Zinc and copper pyrithione are useful as antimicrobial agents active against gram-positive and negative bacteria, fungi, and yeasts. Zinc pyrithione is used as an antidandruff component in shampoos, while technical suspensions of zinc pyrithione and/or copper pyrithione are used as preservatives in paints and polymers. Synthesis of polyvalent pyrithione salts are described in U.S. Pat. No. 2,809,971 to Berstein et al. Other patents disclosing similar compounds and processes for making them include U.S. Pat. Nos. 2,786,847; 3,589,999; 3,590,035; 3,773,770.

Known methods for producing insoluble polyvalent salts of pyrithione result in platelet-shaped large particles having an average size greater than 2 micrometers ($\mu$m). These particles are either used directly, or converted into smaller spherical particles. Such small spherical particles of pyrithione salts are usually generated by a separate mechanical manipulation step (e.g., grinding or crushing) on larger particles or crystals that are made by conventional processes. For example, European Patent Application No. 70046 describes preparation of zinc pyrithione using organic solvents. This process results in production of large crystals of zinc pyrithione. A separate, optional grinding step is used to grind the large crystals and produce zinc pyrithione particles of smaller size. Small spherical particles of zinc pyrithione more easily form suspensions and provide a larger surface area for enhanced biocidal activity. However, grinding larger particles to produce smaller particles, as described in the prior art, generally results in substantial loss of useful product and are costly in terms of equipment, time, and energy required. In addition, alternative forms of pyrithione particles, such as rods, needles, or other shapes, cannot be produced by grinding.

Alternative forms of insoluble polyvalent pyrithione particles are often desirable because they offer certain physical properties that are not inherent in platelet or spherical forms. Elongated particles of pyrithione salts, such as rods, needles, ellipsoids, and the like offer advantages such as a large and/or flat surface area for use in shampoos, soaps and paints. In addition, elongated particles are more easily isolable by conventional filtration methods than the platelet particles of the prior art.

U.S. Pat. No. 5,540,860 to Hosseini et al. discloses a general method for producing several forms of copper pyrithione particles, such as rods, spheres, needles, platelets, and combinations thereof at processing temperatures of about 70° C. or greater by using a variety of surfactants including POLYTERGENT 2A-1L, POLYTERGENT SLF-18, and TRITON X-100 surfactants. However, a general method of producing non-platelet or non-spherical forms of pyrithione salts at lower temperatures and with other salts is not disclosed.

U.S. Pat. No. 5,650,095 to Hosseini et al. also discloses a general method for producing several forms of copper pyrithione particles, such as rods, spheres, needles, platelets, and combinations thereof at processing temperatures between 25 and 90° C. and in a pH range from 3 to 8 by using a variety of surfactants including POLYTERGENT 2A-1L, POLYTERGENT SLF-18, and TRITON X-100 surfactants. However, like the '860 patent above, this patent does not disclose a general method of producing non-platelet or non-spherical forms of pyrithione salts.

Thus, what is needed in the art is a general method of generating non-spherical or non-platelet particles of pyrithione salts in a single step production process at low temperatures. The present invention is believed to be an answer to that need.

SUMMARY OF THE INVENTION

In one aspect, the invention relates to a method for producing non-spherical and/or non-platelet particles of pyrithione salt selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, comprising reacting pyrithione acid or a water-soluble salt of pyrithione and a polyvalent water-soluble metal salt selected from the group consisting of zinc salts, tin salts, cadmium salts, bismuth salts, zirconium salts, magnesium salts, aluminum salts, and combinations thereof, in a carrier and in the presence of an ionic surfactant composition, at a temperature from about 20° C. to about 60° C. and a pH between 4 and 9, to produce non-spherical and non-platelet particles of pyrithione salt.

In another aspect, the invention relates to non-spherical and/or non-platelet particles of divalent pyrithione salt, the divalent pyrithione salt selected from the group consisting of zinc pyrithione salts, tin pyrithione salts, cadmium pyrithione salts, bismuth pyrithione salts, zirconium pyrithione salts, magnesium pyrithione salts, and combinations thereof, and made by reacting pyrithione acid or a water-soluble salt of pyrithione and a water-soluble divalent metal salt in a carrier and in the presence of an ionic surfactant composition, at a temperature from about 20° C. to about 60° C. and a pH of between 4 and 9, to produce non-spherical and/or non-platelet particles of divalent pyrithione salts, the non-spherical and/or non-platelet particles of divalent pyrithione salt having a configuration selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof.

In still another aspect, the present invention relates to a method for producing elongated particles of zinc pyrithione selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, comprising reacting pyrithione acid or a water-soluble salt of pyrithione and a water-soluble zinc salt selected from the group consisting of zinc sulfate, zinc chloride, zinc acetate, and combinations thereof, in an aqueous medium and in the presence of an ionic surfactant composition comprising from about 0.1 to about 5 wt %, based on the total weight of the pyrithione or a water-soluble salt of pyrithione, and selected from the group consisting of one or more ionic surfactants selected from the group consisting of cationic surfactants, anionic surfactants, zwitterionic surfactants, and combinations thereof, and a combination of the ionic surfactants and one or more nonionic surfactants, at a temperature from about 20° C. to 60° C. and pH from about 4 to about 9, to produce elongated particles of zinc pyrithione, the elongated particles having an aspect ratio of from about 2 to about 100.

In yet another aspect, the present invention relates to stable non-spherical and/or non-platelet particles of divalent pyrithione salt, the divalent pyrithione salt selected from the group consisting of zinc pyrithione salts, tin pyrithione salts, cadmium pyrithione salts, bismuth pyrithione salts, zirconium pyrithione salts, magnesium pyrithione salts, and combinations thereof, and having a shape selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, that are physically stable against thermal degradation up to a temperature of 60° C., the particles being made by reacting a reaction mixture comprising pyrithione acid or a water-soluble salt of pyrithione and a water-soluble divalent metal salt in a carrier and in the presence of an ionic surfactant composition comprising from about 0.1 to about 5 wt %, based on the total weight of the pyrithione or a water-soluble salt of pyrithione, while stirring the reaction mixture at a mixing speed of less than 150 rpms.

In still another aspect, the invention relates to A composition, comprising (1) non-spherical and/or non-platelet particles of pyrithione salt selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, made by the method of claim 1; and (2) an ionic surfactant composition, comprising one or more ionic surfactants selected from the group consisting of cationic surfactants, anionic surfactants, zwitterionic surfactants, or a combination of at least one of the ionic surfactants and at least one nonionic surfactant.

These and other aspects will become apparent upon reading the following detailed description of the invention.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
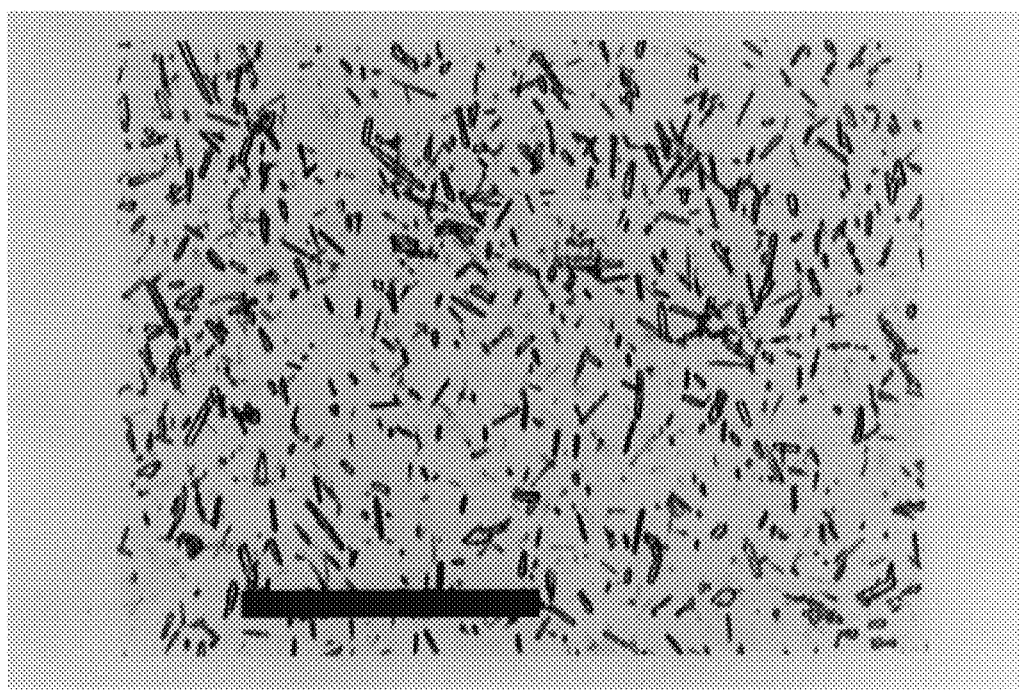
FIG. 1 is a photomicrograph of rods and/or needles of zinc pyrithione prepared by the method of the invention viewed at 340×magnification.

It now has been surprisingly found, in accordance with the present invention, that a solution is provided to the problem of producing pyrithione salt particles in forms other than platelet or spherical form, such as rods, needles, cylinders, cones, ellipsoids, prisms, parallelepipeds, pyramids, cubes, and the like. The present inventors have solved this problem utilizing a surfactant composition as herein defined, and a range of processing temperatures and pH which promote the formation of non-platelet forms of pyrithione salt particles. In one embodiment, pyrithione salt particles having an elongated form, such as rods or needles, may be produced in accordance with the method of the present invention. The elongated pyrithione salt particles made by the method of the invention have excellent surface deposition properties due to the large surface area of the elongated particles. This large surface area results in improved biocidal efficacy in shampoos, soaps and paints. In addition, the elongated particles made according to the method of the invention are more easily isolable by conventional filtration methods than the platelet or spherical particles of the prior art.

As used herein, the term "water-soluble salts of pyrithione" or "water-soluble pyrithione salts" include those salts of pyrithione in which the hydrogen atom of the thiol group is substituted with a monovalent cation. The term "water-soluble polyvalent metal salt" refers to those water-soluble salts in which the cation has a charge of +2 or greater. The term "non-platelet" refers to any form other than platelet form. The term "elongated" is defined herein as any form having an aspect ratio greater than about 1.0, for example, rods, needles, or ellipsoids. As defined herein, the term "aspect ratio" means the ratio of length to width (L:W). The terms "particles of pyrithione salts" or "pyrithione salt particles" as used herein refer to those salts of pyrithione that form precipitates and are essentially insoluble or sparingly soluble in the surrounding medium. The term "induce" as used herein refers to any cause that results in morphological change of the non- spherical and non-platelet particles of the invention, for example, changes in temperature, pH, or pressure. The term "morphological transformation" is used herein to refer to the process of changing from one crystalline form to another crystalline form, for example, from elongated particles to small platelets. The term "more stable form" refers to a thermodynamically more stable form than non-spherical and non- platelet particles. The term "metastable" refers to a crystalline state that may be altered by application of external environmental factors.

The term "surfactant" as used herein refers to any compound that reduces surface tension when dissolved in water or water solutions, or which reduces interfacial tension between two liquids, or between a liquid and a solid, including ionic surfactants and nonionic surfactants. The term "ionic surfactant" refers to those surfactants with at least one charge on the molecule, for example anionic (negatively charged), cationic (positively charged), or zwitterionic (both positively and negatively charged) surfactants, and is distinguished from "nonionic" surfactants wherein no charge is present on the molecule. The phrase "ionic surfactant composition" is expressly defined herein as a combination of one or more ionic surfactants, or a combination of at least one ionic surfactant and at least one nonionic surfactant (e.g. a combination of a nonionic surfactant and an ionic surfactant).

In accordance with the process of the present invention, pyrithione or a water-soluble salt of pyrithione is reacted with a water-soluble salt of a selected polyvalent metal in the presence of the surfactant composition as defined above to form elongated pyrithione salt particles as a precipitate. Each of these components is discussed in more detail below.

Pyrithione in its acid form, or a water-soluble salt of pyrithione may be used in the reaction. Useful water soluble salts of pyrithione preferably include an ammonium ion or an alkali metal ion such as sodium. Accordingly, exemplary water soluble salts of pyrithione include sodium pyrithione, potassium pyrithione, lithium pyrithione, ammonium pyrithione, and combinations of these. The most preferred water-soluble salt of pyrithione useful in the present invention is the sodium salt (i.e., sodium pyrithione). The amount of pyrithione or water-soluble salt of pyrithione can vary over a wide range and establishing a useful amount is within the capabilities of the ordinary skilled practitioner based on the stoichiometry of the reaction and the required amount of particles that must be generated. A preferred amount of pyrithione or water-soluble pyrithione salt is from about 3% to about 52% by weight of the total weight of the reaction mixture.

Exemplary water-soluble polyvalent metal salts useful in accordance with the method of the invention include example zinc salts, tin salts, cadmium salts, copper salts, zirconium salts, magnesium salts, aluminum salts, and the like. Combinations of these salts may also be employed. Useful counterions for these metals include nitrates, acetates, sulfates, halides or combinations thereof. Preferred water-soluble polyvalent metal salts include zinc chloride ($ZnCl_2$), copper chloride ($CuCl_2$), zinc acetate ($Zn(O_2CCH_3)_2$) and zinc sulfate ($ZnSO_4$). The amount of water-soluble polyvalent metal salt can vary depending on the amount of water-soluble salt of pyrithione. The molar ratio of pyrithione or water-soluble salt of pyrithione to the water-soluble polyvalent metal salt is generally in the range from about 2:1 to about 8:1. Preferably, a slight stoichiometric excess (e.g., 5% of water-soluble polyvalent metal salt by weight over pyrithione or water-soluble salt of pyrithione) is desirable to ensure a complete reaction.

As mentioned above, the reaction is conducted in the presence of an ionic surfactant composition made from either one or more ionic surfactants, or a combination of one or more ionic surfactants and one or more nonionic surfactants. Useful ionic surfactants may be selected from the classes of surfactants known as anionics, cationics, and amphoterics (the latter being also commonly referred to as "zwitterionics").

Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates. Useful anionics also include the alkylated diphenyl oxide sulfonates, and their methods of preparation are well-known, as illustrated by the disclosures of U.S. Pat. No. 3,264,242; 3,634,272; and 3,945,437, the disclosures of which are all incorporated herein by reference. Commercial methods of preparation of the alkylated diphenyl oxide sulfonates generally do not produce species which are monoalkylated, monosulfonated, dialkylated or disulfonated. The commercially available species typically are predominately (greater than 90 percent) disulfonated and are a mixture of mono- and di- alkylated with the percentage of dialkylation being about 15 to about 25 percent, and the percentage of monoalkylation being about 75 to 85 percent. Most typically, the commercially available species are about 80 percent monoalkylated and 20 percent dialkylated.

Two illustrative commercially available solutions containing alkylated diphenyl oxide sulfonate surfactants are DOWFAX 8390 and DOWFAX 8390A surfactants, trademarked products of The Dow Chemical Company. In each, the alkyl group is predominantly a hexadecyl $C_{16}$ group. These products are suitably employed in a solution fully or partially neutralized with ammonium hydroxide if desired. An example of a diphenylether disulphonate surfactant is POLY-TERGENT 2A1-L, a trademark of Arch Chemicals, Inc.

An advantageous anionic surfactant is also provided by reacting the above-described alkylated diphenyl oxide sulfonates with a piperazine compound to produce a molar ratio of sulfonate compound to piperazine compound of between about 10:1 and about 1:10, preferably between about 2:1 and about 1:2. Although any piperazine compound can be used for such reaction, preferred compounds include those selected from the group consisting of 1,2-aminoethyl piperazine, 1,4-piperazinediethane sulfonic acid, anhydrous piperazine, hydrated piperazine, and combinations thereof.

Other useful anionics are polycarboxylated alcohol alkoxylates, preferably those selected from acids or organic or inorganic salts of the following: polycarboxylated linear alcohol alkoxylates, polycarboxylated branched alcohol alkoxylates, polycarboxylated cyclic alcohol alkoxylates, and combinations thereof. These polycarboxylated alcohol alkoxylates typically contain at least two succinic acid radicals per molecule. Preferred polycarboxylated alcohol alkoxylates are those having a backbone containing both poly(propylene oxide) and poly(ethylene oxide) blocks, and such preferred polycarboxylated alcohol alkoxylates are readily commercially available, for example, as POLY-TERGENT CS-1, a trademarked surfactant of Arch Chemicals, Inc. If desired, at least a portion of the acid groups on the polycarboxylated alcohol alkoxylate are neutralized with a base to provide the corresponding salt. Suitable bases include alkali metal hydroxides, alkaline earth metal hydroxides, and metal-free hydroxides, including potassium hydroxide, ammonium hydroxide, calcium hydroxide, magnesium hydroxide, ammonia, mono-, di- and tri-ethanol amines, and combinations thereof. Sodium hydroxide is preferred, and although potassium hydroxide can be employed, it is not preferred. The organic or inorganic base is preferably employed in at least an equimolar amount relative to the number of moles of polycarboxylated alcohol alkoxylated used. The polycarboxylated alcohol may also contain a polycarboxylic acid, for example, polyacrylic acid, along with the starting alcohol alkoxylate and esters of the alkoxylate of the polycarboxylic acid.

Illustrative cationic surfactants include alkyl triammonium halide, non-linear alkyl dimethyl halide, alkyl dimethyl benzyl ammonium halide-containing surfactants, cetyltrimethylammonium chloride, and primary alkyl amines (such as ARMEEN surfactant, a product of Akzo Chemical Co.). Illustrative amphoteric surfactants include polyglycol ether derivatives, ethoxylate oxazoline derivatives, lauramidopropyl betaine, lecithin, MIRATAIN CAP-B, a product of Rhone-Poulanc.

Useful nonionic surfactants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. Useful linear alcohol alkoxylates are commercially available, for example, under the registered trademark POLYTERGENT SL-42, a product of Arch Chemicals, Inc. If desired, the alcohol alkoxylate is suitably end-capped with a lower alkyl group, and such a product is commercially available as POLYTERGENT SLF-18, a propylene oxide-capped linear alcohol alkoxylate that is also a product of Arch Chemicals, Inc., and these end-capped linear alcohol alkoxylates are notably low foaming during use. Also advantageous for use in accordance with the present invention are surfactants within the group commercially available as POLYTERGENT SLF-18B series surfactants, which are surfactants characterized by enhanced biodegradability (also products of Arch Chemicals, Inc.), being alkene oxide-capped linear alcohol alkoxylates, containing ethylene oxide moieties in the backbone, and suitably also containing at least one propylene oxide moiety in the backbone, as disclosed, for example, in U.S. Pat. No. 4,925,587 and 4,898,621.

Other useful nonionic surfactants include one commercially available as NEODOL 91-6, a registered trademark surfactant product of Shell Chemical. This surfactant is a detergent range mixture of $C_9$–$C_{11}$, linear primary alcohol ethoxylates having an average of six moles of ethylene oxide per mole of alcohol. Other useful nonionic surfactants include those containing a linear $C_9$–$C_{11}$, carbon chain and five or six ethylene oxide or propylene oxide groups per molecule.

As mentioned above, suitable blends of surfactants can be employed in the process of the present invention to form the ionic surfactant composition, based on various combinations of the above-described surfactants, with the proviso that if one or more nonionic surfactants are used in the surfactant composition, that surfactant composition must also include at least one ionic surfactant. Combinations can include blends of: anionic with anionic, anionic with nonionic, anionic with cationic, anionic with amphoteric, cationic with cationic, cationic with amphoteric, nonionic with amphoteric, and amphoteric with amphoteric. Likewise, ternary and quaternary blends of surfactants may also be used to make the surfactant composition by selecting three or four surfactants, respectively, from within or among the above-described classes.

Suitably, any single or combination of two, three or four surfactants from the following illustrative list are suitably employed in the ionic surfactant composition, with the proviso that if one or more nonionic surfactants are used in the surfactant composition, that surfactant composition must include at least one ionic surfactant: (a) nonionics, including alkoxylated linear alcohols (such as POLYTERGENT SLF-18 surfactant, a product of Arch Chemicals, Inc.), linear alcohol ethoxylates (such as NEODOL 91-8 surfactant, a product of the Shell Corporation), ethoxylated linear alkyl benzene (such as TRITON X-100 surfactant, a product of Union Carbide Corporation), and EO/PO block copolymers (such as POLY-TERGENT E-17A surfactant, a product of Arch Chemicals, Inc.); (b) anionics, including alkyl diphenyl ether disulfonates (such as POLY-TERGENT 2A1 surfactant, a product of Arch Chemicals, Inc.), alkyl phenyl ethoxylated phosphate esters (such as Wayfos M-60 surfactant, a product of Arch Chemicals, Inc.), carboxylated linear alcohol alkoxylates (such as POLY-TERGENT CS-1 surfactant, a product of Arch Chemicals, Inc.), linear alkyl benzene sulfonic acid (such as BIOSOFT S-130 surfactant, a product of Stepan Company), alpha-olefin sulfonates (such as BIO TERG AS-40 surfactant, a product of Stepan Company), dialkylsulfosuccinates (such as AROWET SC-75 surfactant, a to product of Arol Chemical Products), and alkyl sulfates (such as STEPANOL SLS surfactant, a product of Stepan Company); (c) cationics including alkyl triammonium halides (such as CTAB surfactant, a product of VWR Scientific Inc.), alkyl diammonium halides (such as didecyl diammonium chloride sold under the tradename BTC-99 as a product of Stepan); polyoxyethylene cocoamine (such as MAZEEN surfactant, a product of PPG Industries), primary alkyl amines (such as ARMEEN surfactant, a product of Akzo Chemical Co.), dicoco dimethyl ammonium halide (such as JET QUAT surfactant, a product of Jetco Chemical Inc.), di-isodecyl dimethyl ammonium halides (such as AMMONYX K9 surfactant, a product of Stepan Company), and diethyl aminoethyl stearate (such as CERASYNT 303 surfactant, a product of ISP Van Dyke); and, (d) amphoterics, including polyglycol ether derivatives (such as ALBEGAL A surfactant, a product of Ciba-Geigy), ethoxylated oxazolin derivatives (such as ALKATERG T-IV surfactant, a product of Angus Chemicals), lauramide propyl betain (such as LEXAINE C surfactant, a product of Inolex Chemicals), lecithin (such as CANASPERSE surfactant, a product of Can Amoral), disodium cocoamphodiacetate (such as MONATERICS surfactant, a product of Mona Industries), complex fatty amine salt (such as MAFO 13 surfactant, a product of PPG Industries), and cocoamine oxide (such as MACKAMINE CO surfactant, a product of the McIntyre Group Ltd.).

The ionic surfactant composition is preferably employed in the composition of the invention in a range from about 0.1 to about 5 wt %, more preferably from about 0.8 to about 1.2 wt %, based on the total weight of the pyrithione or water-soluble salt of pyrithione. A particularly preferred amount of the surfactant composition is 1 wt %, based on the total weight of the pyrithione or water-soluble salt of pyrithione.

Within the ionic surfactant composition, if more than one surfactant is employed in the composition, each surfactant may range from 1 wt % to 99 wt %, based on the total weight of the surfactant composition. Water or another suitable solvent may optionally be used to dilute the surfactant composition. In one embodiment, a surfactant composition made from 50 wt % of Poly-Terg CS-1 (an anionic surfactant) and 50 wt % Poly-Terg 2A1-L (another anionic surfactant) may be employed. In another embodiment, a surfactant composition made from 25 wt % of Poly-Terg 2A1-L (an anionic surfactant), 25 wt % Triton X-100 (a nonionic surfactant), 12.5 wt % Poly-Terg SLF-18 (an anionic surfactant), and 37.5 wt % water, may be employed.

Useful media or carriers for the reaction include aqueous media such as water, or water in combination with one or more organic solvent(s). Useful organic solvents include alcohols, such as methanol, ethanol, amines such as diethanolamine, ether, esters, and the like. Additional salts, such as potassium chloride, sodium chloride, magnesium chloride, and the like may also be added to the reaction medium to control particle length and shape. Addition of these salts result in elongated particles having a flatter appearance. Preferably, the additional salts are included in the reaction mixture in an amount of from 0.1% by weight to about 10% by weight, more preferably from about 1% by weight to about 8% by weight, and most preferably from about 3% by weight to about 6% by weight, all based on the total weight of the reaction mixture. A particularly useful amount of additional sodium chloride added to the reaction mixture to control particle size and shape is 5% by weight based on the total weight of the reaction mixture.

A dispersant may be included in the reaction mixture to promote formation of elongated particles of pyrithione salt as disclosed in co-pending U.S. Ser. No. 09/025,665, herein incorporated by reference in its entirety. Preferably, the dispersant is a salt of polymerized alkyl naphthalene sulfonic acids, such as "DARVAN 1" (sodium naphthalene sulfonic acid formaldehyde, a product of R. T. Vanderbilt Co. Inc.), "DEMOL N" (sodium salt of naphthalene sulfonic acid, a product of Kao Chemicals), "DAXAD 11" (sodium salt of polymerized alkyl naphthalene sulfonic acids, a product of W. R. Grace & Co.), "TAMOL N" (sodium salt of condensed naphthalene sulfonic acid, a product of Rohm and Haas Co.), "HAROL KG" (potassium salts of polymerized alkyl naphthalene sulfonic acids, a product of Graden Chemical Co.), "HAROL RG-71" (sodium salts of polymerized alkyl naphthalene sulfonic acids, a product of Graden Chemical Co.), "LOMAR LS" (sodium salt of condensed mononaphthalene sulfonic acid, a product of Henkel Corp.) and the like. Additional useful dispersants are disclosed in McCutcheons Handbook of Functional Materials (North American Volume I, 1992) which is incorporated by reference in its entirety herein. Combinations of two, three, four, or more dispersants as described herein may also be used according to the invention. The dispersant is preferably employed in a total amount of between about 0.05 and 10%, more preferably between about 0.1 and 5%, most preferably between about 0.5 and about 1.5% by weight, based on the total weight of the reaction mixture.

Pearlizing agents, such as $TiO_2$-coated mica, may also be included to promote particle growth. Generally, these optional ingredients comprise from about 0.1 to about 20% by weight, more preferably from about 1 to about 15% by weight, and most preferably from about 1 to about 6% by weight, all based on the total weight of the reaction mixture.

The temperature of the reaction may be any temperature which permits precipitation of elongated particles of pyrithione salt. Preferable temperatures for the reaction are in the range of from between about 20° C. and about 60° C., and more preferably between about 30° C. and about 55° C. The pH of the reaction is preferably in the range from 4–9, and more preferably in the range of from 6–8. In addition, the reaction may be gently agitated to promote formation of elongated particles. Stirring at high rpm of greater than 150 rpm tends to produce metastable particles that can be induced to undergo a morphological transformation to more stable small particles having sizes about 1 $\mu$m or less by perturbing the environment of the particles. Generally, gently stirring the reaction at 150 rpm or less, and preferably about 100 rpm, most preferably from 50 to 100 rpm, is sufficient to promote formation of elongated particles that are physically stable against thermal degradation up to 60° C.

In order to produce the elongated particles of the invention, pyrithione or a selected water-soluble salt of pyrithione and a selected water-soluble polyvalent metal salt are reacted in the presence of a surfactant composition as defined herein in any suitable reaction vessel at a temperature below 70° C., and preferably between about 20° C. and 60° C. The particles formed by the method of the invention can take any nonspherical or non-platelet form, such as rods, needles, cylinders, cones, ellipsoids, prisms, parallelepipeds, pyramids, and the like. The particles formed by the present invention may also take the form of tetrahedrons, hexahedrons (cube), octahedrons, dodecahedrons, icosahedrons, and the like.

Figure 2:
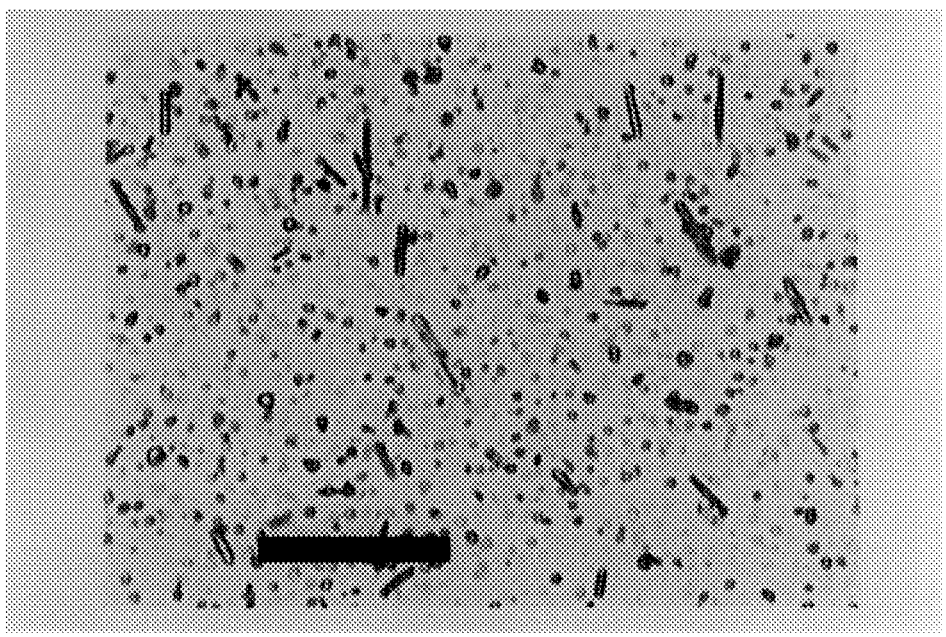
FIG. 2 is a photomicrograph of rods and/or needles of zinc pyrithione prepared by the method of the invention viewed at 680×magnification.

In a preferred embodiment, sodium pyrithione is reacted with zinc chloride or zinc sulfate in the presence of a surfactant composition as herein defined about 35° C. to form zinc pyrithione having rod and/or needles shapes, along with aqueous by-products. The method of the invention may also be utilized in a "continuous" process in which the zinc pyrithione particles are collected, and the mother liquor containing aqueous by-products is recycled back to the reaction vessel. An optional filter (e.g., carbon or charcoal filter) may be employed to remove impurities such as colored organic compounds from the mother liquor. Particles of zinc pyrithione so formed have a "needle" and/or "rod" appearance as shown in FIGS. 1 and 2. Generally, the rods or needles of zinc pyrithione salt produced in accordance with the present invention are between about 0.1 and about 1 $\mu$m in width and between about 2 and about 50 $\mu$m in length. Accordingly, the aspect ratio of the elongated particles is greater than about 1, and more preferably from about 2 to about 100.

The non-spherical and/or non-platelet pyrithione salt particles produced by the method of the invention at a mixing speed of greater than 150 rpm have been observed to undergo a morphological transformation to small particles when the particles are subjected to certain external environmental factors. While not wishing to be bound by any particular theory, the applicants postulate that the non-spherical and/or non-platelet particles produced by the method of the invention at rpm greater than 150 rpm are in a metastable state and can be induced to undergo a morphological transformation to more stable small particles having sizes about 1 $\mu$m or less by perturbing the environment of the particles. Accordingly, it is the Applicants' intention to cover all those more stable crystalline forms that result from morphological transformation of the metastable particles in accordance with the present invention.

The particles produced according to the method of the invention are useful in a variety of items such as personal care products (soaps, shampoos, skin-care medicaments, and the like), paints, coatings, fertilizers, and foodstuffs. For example, zinc pyrithione particles made according to the method of the invention are a useful antidandruff additive to antidandruff shampoos.

Alternatively, the mixture of particles and by-products may be added to commercial products directly without further purification. Illustratively, the by-products (e.g., aqueous sodium chloride or aqueous sodium sulfate) are useful in shampoo or soap formulations as thickeners. An additional benefit derived from the needle/rod shape is the ease of separation of these particles from the reaction medium.

The following examples are intended to illustrate, but in no way limit the scope of the present invention. All parts and percentages are by weight and all temperatures are in degrees Celsius unless explicitly stated otherwise. "q.s." refers to "quantity sufficient".

EXAMPLES 1–9

Production and Analysis of Needles of Zinc Pyrithione

In the following Examples, 2,000 grams of a 10% (by weight) aqueous sodium pyrithione solution was combined with approximately 463 grams of a 20% (by weight) aqueous zinc chloride solution in the presence of various surfactant compositions as defined above and shown in Table I. Approximately 1 wt % of the surfactant composition was added to each reaction (based on the total weight of the sodium pyrithione). 0.125 wt % (based on total sodium pyrithione weight (2.5 grams)) of sodium meta bisulfate was added to each reaction. The zinc chloride solution was added over approximately 90 minutes, and the reaction was maintained at approximately 30° C. (±2° C.). The pH of the reaction was maintained between 7.0 and 7.5. The results of each reaction are described in Table I.

TABLE I

| Example | Surfactant Composition (Components expressed as wt %) | Type | Morphology |
|---|---|---|---|
| 1 | Poly-Terg 2A1-L (25%) | Anionic | Mix of needle and rod-type crystals of varying sizes. |
|  | Triton X100 (25%) | Nonionic |  |
|  | Poly-Terg SLF-18 (12.5%) | Nonionic |  |
|  | $H_2O$ (37.5%) |  |  |
| 2 | Cetyltrimethylammonium Chloride (100%) | Cationic | Mix of small needles and rods, along with non needle or rod |
| 3 | Surfonic LF-17 | Nonionic | Mix of needles and rods |
|  | BTC-99 | Cationic |  |
|  | Triton X100 | Nonionic |  |
|  | $H_2O$ |  |  |
| 4 | Poly-Terg CS-1 (50%) | Anionic | Mixture of both needles and rods, and non-needle or rod forms |
|  | Poly-Terg 2A1-L (50%) | Anionic |  |
| 5 | Armeen DM12D | Cationic | Mostly small non-needle or rod forms |
| 6 | Miratain CAP-B | Amphoteric | Small needles and rods, some in crystal form. |
| 7 (Com-parative) | Alkamide CDE (100%) | Nonionic | Mix of non-needle and non-rod forms. |
| 8 (Com-parative) | Triton X100 (25%) | Nonionic | Undeterminable morphology including non-needle and non-rod forms |
|  | Surfynol DF75 (25%) | Nonionic |  |
|  | $H_2O$ (50%) |  |  |
| 9 (Com-parative) | Neodol 91-8 (100%) | Nonionic | Agglomerated particles, no needles or rods. |

As shown in Table I, Examples 1–6 produce rod and needle forms of solid pyrithione salts using a surfactant composition made from one or more ionic surfactants, or a combination of at least one ionic surfactant and at least one nonionic surfactant. In contrast, Examples 7–9, using only nonionic surfactants in the surfactant composition, produce agglomerated particles or non-needles or non-rods, and not the desired rods or needles.

The rods and needles of solid zinc pyrithione produced in Examples 1–6 may be used in various shampoo formulations as illustrated in Examples 10–14 below.

EXAMPLE 10

Proposed Example
Antidandruff Shampoo Formulation I

An antidandruff shampoo composition is made using needle and rod forms of zinc pyrithione made as described in Examples 1–6 in combination with the following ingredients:

| Component A: | |
|---|---|
| Water | 41.0% |
| Magnesium aluminum silicate | 1.0% |
| Hydroxypropyl methylcellulose | 0.8% |
| Component B: | |
| Zinc Pyrithione (needles/rods, 25% aqueous dispersion) | 4.0% |
| Component C: | |
| Cocamide DEA | 1.0% |
| Component D: | |
| Triethanolamine lauryl sulfate, 40% | 40.0% |
| Triethanolamine, 99% | 3.2% |
| FD&C Blue No. 1 (0.2%) | 1.5% |
| FD&C Yellow No. 5 (0.1%) | 0.5% |
| Fragrance | q.s. |

The antidandruff shampoo composition is made as follows:

Component A is prepared by heating water to 70° C. and dissolving the other two components with stirring (about 1500 rpm). The temperature of the mixture is lowered to 5° C., and component B is added, and stirring continued for 5 minutes. Stirring speed is reduce stirring to ~300 rpm. Component C is melted in a separate container, and added to the A/B mixture. The heat is removed and component D is added while the mixture cooled.

EXAMPLE 11

Proposed Example
Second Antidandruff Shampoo

A second antidandruff shampoo composition is made using needle and rod forms of zinc pyrithione made as described in Examples 1–6 in combination with the following ingredients:

| Component A: | |
|---|---|
| Deionized water | 76.0% |
| Ammonium lauryl sulfate | 15.0% |
| Cocamide DEA | 2.0% |
| Component B: | |
| Di(hydrogenated) tallow phthalic acid amide | 5.0% |
| Zinc Pyrithione (needles/rods, 25% aqueous dispersion) | 4.0% |
| Component C: | |
| Preservative | q.s. |
| Component D: | |
| Citric Acid, 50% aq.Solution, OR Sodium hydroxide, 50% aqueous solution | q.s. |
| Component E: | |
| Ammonium chloride | q.s. |

The antidandruff shampoo composition is made as follows:

In separate containers, components A and B are each mixed well. Component A is heated to 60° C. and component B is added. The mixture is stirred for 30 minutes. The mixture is then cooled to 50° C., and component C is added. The pH of the resulting mixture is adjusted to 5.0–6.2 with component D, and the viscosity is adjusted with component E.

EXAMPLE 12

Proposed Example
Conditioning Antidandruff Shampoo

An antidandruff shampoo and conditioner composition is made using needle and rod forms of zinc pyrithione made as described in Examples 1–6 in combination with the following ingredients:

| Component A: | |
|---|---|
| Deionized Water | 77.0% |
| Ammonium lauryl sulfate | 20.0% |
| Cocamide DEA | 2.0% |
| Component B: | |
| Di(hydrogenated) tallow phthalic acid amide | 4.0% |
| Zinc Pyrithione (needles/rods, 25% aqueous dispersion) | 4.0% |
| Dimethicone, 12,000 cps | 0.5% |
| Component C: | |
| Preservative | q.s. |
| Component D: | |
| Citric acid, 50% aqueous solution, OR Sodium hydroxide, 50% aqueous solution | q.s. |
| Component E: | |
| Ammonium chloride | q.s. |

The antidandruff shampoo and conditioner composition is made as follows:

In separate containers, components A and B were each mixed well. Component A is heated to 60° C. and component B is added. The mixture is stirred for 30 minutes. The mixture is then cooled to 50° C., and component C is added. The pH of the resulting mixture is adjusted to 5.0–6.2 with component D, and the viscosity is adjusted with component E.

EXAMPLE 13

Proposed Example
A Second Conditioning Antidandruff Shampoo

Another antidandruff shampoo and conditioner composition is made using needle and rod forms of zinc pyrithione made as described in Examples 1–6 in combination with the following ingredients:

| Component A: | |
|---|---|
| Deionized water | 21.75% |
| Guar hydroxypropyl trimonium chloride | 0.30% |
| Magnesium Aluminum Silicate | 0.70% |
| Zinc Pyrithione (needles/rods, 25% aqueous dispersion) | 4.0% |
| Component B: | |
| Sodium laureth sulfate | 30.0% |
| Ammonium xylene sulfonate, 40% aq. | 02.0% |
| Component C: | |
| Tricetylammonium chloride | 0.50% |
| Cetyl alcohol NF | 0.40% |
| Stearyl alcohol | 0.40% |
| lycol distearate | 2.00% |
| Component D: | |
| Cocamide MEA | 1.70% |
| Ammonium lauryl sulfate | 36.00% |
| Component E: | |
| Preservative | 0.05% |
| Fragrance and dye | q.s. |
| Component F | |
| Citric acid, 25% aqueous solution | q.s. |

The antidandruff shampoo and conditioner composition is made as follows:

Component A is prepared by heating water to 50° C. and dispersing the guar hydroxypropyl trimonium chloride and the magnesium aluminum silicate with rapid agitation. The zinc pyrithione dispersion is added to this combination with stirring. The pH of component A is adjusted to 4.5–5.0 with component F. Both components of B were slowly added to component A, mixing well. The pH of the mixture is adjusted to 5.7–6.3 with component F. In a separate container, component C is heated to 70–75° C. The A/B mixture is heated to 60° C. and blend with component C, mixing well. Both components of D were added to the hot mixture, and stirred well. The pH of the mixture is adjusted to 5.7–6.3 with component F. The mixture is cooled to 40–45° C., and component E is added with stirring. If desired, the viscosity of the product can be increased by adding 0.05–1% sodium chloride.

EXAMPLE 14

Proposed Example
"Extra Body" Antidandruff Shampoo

An "extra body" antidandruff shampoo and conditioner composition is made using needle and rod forms of zinc pyrithione made as described in Examples 1–6 in combination with the following ingredients:

| Component A: | |
|---|---|
| Deionized Water | 62.6% |
| Zinc Pyrithione (needles/rods, 25% aqueous dispersion) | 4.0% |
| Component B: | |
| Methyl Paraben | 0.30% |
| Propyl Paraben | 0.10% |
| Propylene Glycol | 0.50% |
| Sodium Chloride | 0.50% |
| Component C: | |
| Triethanolamine lauryl sulfate | 20.0% |
| Cocamide MEA | 4.0% |
| Ethylene glycol distearate | 7.0% |
| Component D: | |
| Cocodimonium hydrolyzed animal protein | 1.00% |
| Component E: | |
| FD&C Blue No. 1 | q.s. |
| Component F: | |
| Citric Acid, 50% aqueous solution | q.s. |

The antidandruff shampoo and conditioner composition is made as follows:

Component A is heated to 60° C. The ingredients of component B were added with good stirring until dissolved. The ingredients of component C were added to the mixture sequentially, and heated with mixing at 60° C. The mixture is cooled with stirring to 40° C., and components D and E were added with stirring. The pH of the final composition is adjusted to 4.7 with component F.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A method for producing non-spherical and/or non-platelet particles of pyrithione salt selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, comprising reacting pyrithione acid or a water-soluble salt of pyrithione and a polyvalent water-soluble metal salt selected from the group consisting of zinc salts, tin salts, cadmium salts, bismuth salts, zirconium salts, magnesium salts, aluminum salts, and combinations thereof, in a carrier and in the presence of an ionic surfactant composition, at a temperature from about 20° C. to about 60° C. and a pH between 4 and 9, to produce non-spherical and non-platelet particles of pyrithione salt.

2. The method of claim 1, wherein said water-soluble salt of pyrithione is selected from the group consisting of sodium pyrithione, potassium pyrithione, lithium pyrithione, ammonium pyrithione, and combinations thereof.

3. The method of claim 1, wherein said polyvalent water-soluble metal salt is a divalent water-soluble metal salt selected from the group consisting of zinc sulfate, zinc chloride, zinc acetate, copper chloride, bismuth acetate, and combinations thereof.

4. The method of claim 1, employing a molar ratio of said pyrithione or water-soluble salt of pyrithione to said water-soluble polyvalent metal salt is in the range from about 2:1 to about 8:1.

5. The method of claim 1, wherein said ionic surfactant composition comprises one or more ionic surfactants selected from the group consisting of cationic surfactants, anionic surfactants, zwitterionic surfactants, or a combination of at least one of said ionic surfactants and at least one nonionic surfactant.

6. The method of claim 1, wherein said ionic surfactant composition comprises from about 0.1 to about 5 wt %, based on the total weight of said pyrithione or water-soluble salt of pyrithione.

7. The method of claim 6, wherein said ionic surfactant composition comprises from about 0.8 to about 1.2 wt %, based on the total weight of said pyrithione or water-soluble salt of pyrithione.

8. The method of claim 7, wherein said ionic surfactant composition comprises from about 1 wt %, based on the total weight of said pyrithione or water-soluble salt of pyrithione.

9. The method of claim 1, wherein said pH is between 6 and 8.

10. The method of claim 1, further comprising the step of isolating said particles of pyrithione salt.

11. The method of claim 1, wherein said non-spherical and/or non-platelet particles of pyrithione salt are elongated and have an aspect ratio of from about 2 to about 100.

12. The method of claim 11, wherein said non-spherical and/or non-platelet particles of pyrithione salt are from about 0.1 to about 1 µm in width and from about 2 to about 50 µm in length.

13. The method of claim 1, further comprising the step of inducing said non-spherical and/or non-platelet particles of pyrithione to undergo a morphological transformation to a more stable form comprising platelets having sizes of about 1 µm or less.

14. Non-spherical and/or non-platelet particles of divalent pyrithione salt, said divalent pyrithione salt selected from the group consisting of zinc pyrithione salts, tin pyrithione salts, cadmium pyrithione salts, bismuth pyrithione salts, zirconium pyrithione salts, magnesium pyrithione salts, and combinations thereof, and made by reacting pyrithione acid or a water-soluble salt of pyrithione and a water-soluble divalent metal salt in a carrier and in the presence of an ionic surfactant composition, at a temperature from about 20° C. to about 60° C. and a pH of between 4 and 9, to produce non-spherical and/or non-platelet particles of divalent pyrithione salts, said non-spherical and/or non-platelet particles of divalent pyrithione salt having a configuration selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof.

15. The non-spherical and/or non-platelet particles of divalent pyrithione salts of claim 14, wherein said non-spherical and/or non-platelet particles of pyrithione are metastable and are further altered by a morphological transformation to a more stable form, said more stable form comprising platelets having sizes about 1 µm or less.

16. A personal care composition, comprising non-spherical and/or non-platelet particles of pyrithione salts made according to claim 14.

17. The personal care composition of claim 16, wherein said personal care composition is selected from the group consisting of soaps, shampoos, and skin-care medicaments.

18. A method for producing elongated particles of zinc pyrithione selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, comprising reacting pyrithione acid or a water-soluble salt of pyrithione and a water-soluble zinc salt selected from the group consisting of zinc sulfate, zinc chloride, zinc acetate, and combinations thereof, in an aqueous medium and in the presence of one or more ionic surfactants comprising from about 0.1 to about 5 wt %, based on the total weight of said pyrithione or a water-soluble salt of pyrithione, and selected from the group consisting of cationic surfactants, anionic surfactants, zwitterionic surfactants, and combinations thereof, or a combination of said ionic surfactants and one or more nonionic surfactants, at a temperature from about 20° C. to 60° C. and pH from about 4 to about 9, to produce elongated particles of zinc pyrithione, said elongated particles having an aspect ratio of from about 2 to about 100.

19. The method of claim 18, wherein said water-soluble salt of pyrithione is selected from the group consisting of sodium pyrithione, potassium pyrithione, lithium pyrithione, ammonium pyrithione, and combinations thereof.

20. The method of claim 19, wherein said ionic surfactant composition comprises from about 0.8 to about 1.2 wt %, based on the total weight of said pyrithione or water-soluble salt of pyrithione.

21. The method of claim 20, wherein said ionic surfactant composition comprises about 1 wt %, based on the total weight of said pyrithione or water-soluble salt of pyrithione.

22. The method of claim 18, further comprising the step of isolating said elongated particles of zinc pyrithione.

23. The method of claim 18, wherein said elongated particles of pyrithione salt are from about 0.1 to about 1 µm in width and from about 2 to about 50 µm in length.

24. The method of claim 18, further comprising the step of inducing said elongated particles of pyrithione to undergo a morphological transformation to a more stable form comprising platelets having sizes about 1 µm or less.

25. Stable non-spherical and/or non-platelet particles of divalent pyrithione salt, said divalent pyrithione salt selected from the group consisting of zinc pyrithione salts, tin pyrithione salts, cadmium pyrithione salts, bismuth pyrithione salts, zirconium pyrithione salts, magnesium pyrithione salts, and combinations thereof, and having a shape selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, that are physically stable against thermal degradation up to a temperature of 60° C., said particles being made by reacting a reaction mixture comprising pyrithione acid or a water-soluble salt of pyrithione and a water-soluble divalent metal salt in a carrier and in the presence of an ionic surfactant composition comprising from about 0.1 to about 5 wt %, based on the total weight of said pyrithione or a water-soluble salt of pyrithione, while stirring said reaction mixture at a mixing speed of less than 150 rpms.

26. The stable non-spherical and/or non-platelet particles of divalent pyrithione salt of claim 25, wherein said water-soluble salt of pyrithione is selected from the group consisting of sodium pyrithione, potassium pyrithione, lithium pyrithione, ammonium pyrithione, and combinations thereof.

27. The stable non-spherical and/or non-platelet particles of divalent pyrithione salt of claim 25, wherein said divalent water-soluble metal salt is a divalent water-soluble metal salt selected from the group consisting of zinc sulfate, zinc chloride, zinc acetate, copper chloride, bismuth acetate, and combinations thereof.

28. The stable non-spherical and/or non-platelet particles of divalent pyrithione salt of claim 25, wherein said ionic surfactant composition comprises one or more ionic surfactants selected from the group consisting of cationic surfactants, anionic surfactants, zwitterionic surfactants, or a combination of at least one of said ionic surfactants and at least one nonionic surfactant.

29. The stable non-spherical and/or non-platelet particles of divalent pyrithione salt of claim 25, wherein said ionic surfactant composition comprises from about 0.1 to about 5 wt %, based on the total weight of said pyrithione or water-soluble salt of pyrithione.

30. The stable non-spherical and/or non-platelet particles of divalent pyrithione salt of claim 29, wherein said ionic surfactant composition comprises from about 0.8 to about 1.2 wt %, based on the total weight of said pyrithione or water-soluble salt of pyrithione.

31. The stable non-spherical and/or non-platelet particles of divalent pyrithione salt of claim 30, wherein said ionic surfactant composition comprises from about 1 wt %, based on the total weight of said pyrithione or water-soluble salt of pyrithione.

32. The stable non-spherical and/or non-platelet particles of divalent pyrithione salt of claim 25, wherein said pH is between 6 and 8.

33. The stable non-spherical and/or non-platelet particles of divalent pyrithione salt produced by the method of claim 31 having a particle size of about 1 micron or less.

34. A composition, comprising:

(1) non-spherical and/or non-platelet particles of pyrithione salt selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, made by the method of claim 1; and (2) an ionic surfactant composition, comprising one or more ionic surfactants selected from the group consisting of cationic surfactants, anionic surfactants, zwitterionic surfactants, or a combination of at least one of said ionic surfactants and at least one nonionic surfactant.

* * * * *